United States Patent [19]
Barnett et al.

[11] Patent Number: 5,278,307
[45] Date of Patent: Jan. 11, 1994

[54] PROCESS FOR PREPARING 4-HYDROXYPYRROLO(2,3-D)PYRIMIDINE BASED ANTIFOLATE COMPOUNDS AND INTERMEDIATES

[75] Inventors: Charles J. Barnett, Indianapolis; Thomas M. Wilson, Speedway, both of Ind.

[73] Assignee: Eli Lilly and Company, Indianapolis, Ind.

[21] Appl. No.: 951,483

[22] Filed: Sep. 25, 1992

[51] Int. Cl.$^5$ .................... C07B 41/02; C07D 487/04
[52] U.S. Cl. .................... 544/280; 549/426; 549/427
[58] Field of Search ........................ 544/280

[56] References Cited

U.S. PATENT DOCUMENTS

| | | | |
|---|---|---|---|
| 4,424,369 | 1/1984 | Schmidt | 549/294 |
| 4,997,838 | 3/1991 | Akimoto | 514/258 |

FOREIGN PATENT DOCUMENTS

| | | |
|---|---|---|
| 431953 | 6/1991 | European Pat. Off. |
| 434426 | 6/1991 | European Pat. Off. |

OTHER PUBLICATIONS

Secrist, et al., *J. Org. Chem.*, 43: 3937–3941 (1978).
Ramasamy, et al., *J. Chem. Soc., Chem. Commun.*, 560–562 (1989).
Larock, et al., *J. Org. Chem.*, 55: 407–408 (1990).
Ley et al., *Tetrahedron Letters*, 29: 5433–5436 (1988).
Pezechk, et al., *Tetrahedron Letters*, 27: 3715–3718 (1986).

*Primary Examiner*—Mark L. Berch
*Attorney, Agent, or Firm*—Steven A. Fontana; Leroy Whitaker

[57] ABSTRACT

The present invention provides a process for preparing a 4-hydroxypyrrolo[2,3-d]pyrimidine derivative of the formula

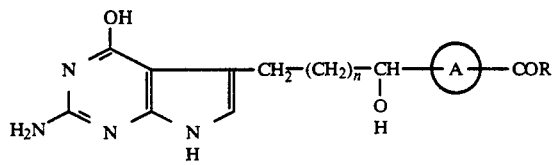

wherein
R is NHC*H(COOR$^1$)CH$_2$CH$_2$COOR$^1$ or OR$^1$;
R$^1$ is H or a carboxyl protecting group;
the configuration about the carbon atom designated * is L;
n is 0 or 1; and
A is an aryl group optionally having, in addition to the COR substituent, one or two substituents selected from the group consisting of halo, hydroxy, C$_1$–C$_4$ alkyl and C$_1$–C$_4$ alkoxy; or a salt thereof, which comprises (a) halogenating a compound of the formula

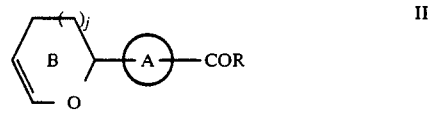

wherein
R, R$^1$, A and * are as defined above;
j is 0 or 1; and (b) reacting 2,4-diamino-6-hydroxypyrimidine, or a salt thereof, with the reaction product from step (a), in the presence of a polar solvent.

21 Claims, No Drawings

PROCESS FOR PREPARING 4-HYDROXYPYRROLO(2,3-D)PYRIMIDINE BASED ANTIFOLATE COMPOUNDS AND INTERMEDIATES

FIELD OF THE INVENTION

This invention relates to the fields of pharmaceutical and organic chemistry, and provides a novel process for the synthesis of 4-hydroxypyrrolo[2,3-d]pyrimidines which are useful as antimetabolites of the antifolate type, and intermediates thereto.

BACKGROUND OF THE INVENTION

Antimetabolites have been used for a number of years as chemotherapeutic agents in the treatment of cancer. One such drug, methotrexate, is now one of the most widely used anticancer drugs; and many other compounds in the folic acid family have been synthesized, tested and discussed in the chemical and medical literature. The compounds have various activities at the enzymatic level; they inhibit such enzymes as dihydrofolate reductase, folate polyglutamate synthetase, glycinamide ribonucleotide formyltransferase and thymidylate synthetase.

More recently, a series of 4-hydroxypyrrolo[2,3-d]pyrimidine-L-glutamic acid derivatives have been disclosed and shown to be particularly useful antifolate drugs. See, for example, U.S. Pat. Nos. 4,996,206; 5,106,974; and 4,997,838. However, the synthetic pathways described therein greatly vary and are frequently inconvenient and complex.

The present invention provides an improved process for the synthesis of intermediates which are useful for the synthesis of 4-hydroxypyrrolo[2,3-d]pyrimidine based antifolate compounds. The process of the present invention is also useful for the synthesis of antifolate compounds which are employed as antineoplastic agents.

Although the intermediate compounds synthesized by the process of this invention are primarily useful for the synthesis of antineoplastic glutamic acid derivatives, one of ordinary skill in the pharmaceutical and organic chemical arts will recognize that the usefulness of these intermediates is not limited to the synthesis of the abovedescribed antineoplastic agents.

SUMMARY OF THE INVENTION

The present invention provides a method for preparing 4-hydroxypyrrolo[2,3-d]pyrimidines of the formula $$\text{OH} \quad \text{I}$$

(structure depicting 4-hydroxypyrrolo[2,3-d]pyrimidine with $\text{CH}_2\text{-(CH}_2\text{)}_n\text{-CH(A)-COR}$ substituent)

wherein
R is $\text{NHC*H(COOR}^1\text{)CH}_2\text{CH}_2\text{COOR}^1$ or $\text{OR}^1$;
$R^1$ is H or a carboxyl protecting group;
the configuration about the carbon atom designated * is L;
n is 0 or 1; and
A is an aryl group; or a salt thereof, which may be substituted; which comprises
(a) halogenating a compound of formula II $$\text{II}$$

(structure of formula II with B ring, A ring, COR substituent)

wherein
R and A are as defined above;
j is 0 to 1; and
(b) reacting 2,4-diamino-6-hydroxypyrimidine; or a salt thereof, with the reaction product from step (a), in the presence of a polar solvent.

DETAILED DESCRIPTION OF THE INVENTION

This invention relates to a process for the synthesis of 4-hydroxypyrrolo[2,3-d]pyridmidines which are useful as antifolate-type antimetabolites, and intermediates thereto.

The compounds of formula I exist in tautomeric equilibrium with the corresponding 4(3H)-oxo compounds. For illustrative purposes, the equilibrium for the pyrrolopyrimidine ring system, and the numbering thereof, are shown below:

(tautomeric equilibrium structures between 4-hydroxy form and 4(3H)-oxo form of pyrrolo[2,3-d]pyrimidine, with ring numbering $N_3$, 2, 1, 7, 6, 5, 4)

For convenience, the 4-hydroxy form is depicted for formula I, and the corresponding nomenclature is used throughout this specification. However, it is understood that such depictions include the corresponding tautomeric 4(3H)-oxo forms.

The ring structure identified as A in formulas I, II and IV is a 5- or 6-members aryl group. The term "aryl" denotes an unsubstituted or substituted aromatic residue, including heterocyclic groups which may have up to three heteroatoms (e.g., N, O and S) contained therein such as, for example, phenyl, thienyl, pyridyl, furyl and the like.

In addition to the COR substituent, the aryl group represented by A in formulas I, II and IV may have one or two substituents, selected from halo, hydroxy, $C_1$–$C_4$ alkyl and $C_1$–$C_4$ alkoxy.

The term "halo" refers to bromo, chloro, fluoro and iodo.

The term "$C_1$–$C_4$ alkyl" refers to the straight or branched aliphatic chains of 1–4 carbon atoms, including methyl, ethyl, propyl, isopropyl, n-butyl, isobutyl, sec-butyl and tert-butyl.

The term "$C_1$–$C_4$ alkoxy" represents a $C_1$–$C_4$ alkyl group attached through an oxygen bridge, such as, for example, methoxy, ethoxy, n-propoxy, isopropoxy and the like.

The carboxyl protecting group of $R^1$, where $R^1$ is not H, denotes a group which generally is not found in the final therapeutic compounds but which is intentionally introduced during a portion of the synthetic process to protect a group which otherwise might react in the course of chemical manipulations, and is then removed at a later stage of the synthesis. Since compounds bearing such a protecting group are of importance primarily as chemical intermediates (although some derivatives also exhibit biological activity), their precise structure is not critical. Numerous reactions for the formation and removal of such protecting groups are described in a number of standard works including, for example, "Protective Groups in Organic Chemistry", Plenum Press, (London and New York, 1973); Greene, Th. W., "Protective Groups in Organic Synthesis", Wiley, (New York, 1981); and "The Peptides", Vol. I, Schroöder and Lubke, Academic Press, (London and New York, 1965).

A carboxyl group can be protected as an ester group which is selectively removable under sufficiently mild conditions so as to not disrupt the desired structure of the molecule. Especially preferred is a lower alkyl ester such as methyl or ethyl. Other lower alkyl esters include those which are branched at the 1-position such as t-butyl, and those which are substituted in the 1- or 2-position with (i) lower alkoxy, such as methoxymethyl, 1-methoxyethyl, ethoxymethyl and the like; (ii) lower alkylthio, such as methylthiomethyl, 1-ethylthioethyl and the like; (iii) halogen, such as 2,2,2-trichloroethyl, 2-bromoethyl, 2-iodoethoxycarbonyl and the like; (iv) 1 to 3 phenyl groups, each of which can be unsubstituted or mono-, di- or tri-substituted with, for example, lower alkyl such as t-butyl, lower alkoxy such as methoxy, hydroxy, halo such as chloro, and nitro such as 4-nitrobenzyl; or (v) aroyl, such as phenacyl.

The starting materials represented by compounds of formula II can be prepared as shown below in Scheme I Scheme I

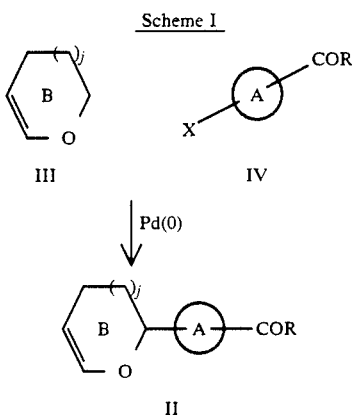

wherein
j is 0 or 1;
A is an aryl group which may be substituted;
X is bromo or iodo;
R is NHC*H(COOR$^1$)CH$_2$CH$_2$COOR$^1$ or OR$^1$;
R$^1$ is H or a carboxyl protecting group;
the configuration about the carbon atom designated * is L.

The methods of preparing compounds of formula II, via palladium catalyzed coupling, are commonly known to organic chemists. See, e.g., Larock, et al., *Tetrahedron Letters*, 30: 2603–2606 (1989), Larock, et al., *J. Org. Chem.*, 55: 407–408 (1990).

Preferred formula IV compounds are those wherein A is a 5-membered aryl group, preferably thiophene which is bromo- or iodo-substituted at the 2-position, and further substituted at the 5-position by the COR group. As described above, R is NHC*H(COOR$^1$)CH$_2$CH$_2$COOR$^1$ or OR$^1$; R$^1$ is H or a carboxyl protecting group; and the configuration about the carbon atom designated * is L (L-glutamic acid, when R$^1$ is H).

Especially preferred formula IV compounds are those wherein A is a 6-membered aryl group, preferably phenyl with a bromo or iodo substituent located at the 4-position to the COR group. Thus, the required substituents located on 5-membered aryl groups (represented below by thiophene-2,5-ylene) and 6- membered aryl groups (represented below by phenyl-1,4-ylene) are as follows:

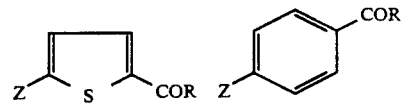

wherein Z is bromo or iodo. Of course, the 5-membered or 6-membered aryl groups may be further substituted as described above.

The second reactant shown in Scheme I, the compound of formula III, is an unsubstituted, oxygen-bearing, 5- or 6-membered ring (the "B-ring"). Compounds of formula III are either commercially available or are prepared by standard methodology well known to those skilled in the art. Preferred formula III compounds are oxacyclopent-2-ene (2,3-dihydro-1H-furan) and oxacyclohexa-5-ene (2,3-dihydro-4H-pyran).

As depicted in Scheme II below, the formula III compound selected as a reactant in Scheme I dictates the length of the carbon bridge between the pyrrolo[2,3-d]pyrimidine moiety and the divalent cyclic group of formula I compounds. The use of 5-membered formula III compounds results in a two-carbon bridge, while the use of 6-membered compounds of formula III results in a three-carbon bridge. In other words, when j in formula II is 0, n in formula I will be 0. Similarly, when j is 1, n will be 1. Thus, the process of this invention provides substantial flexibility when used to synthesis 4-hydroxypyrrolo[2,3-d]pyrimidine intermediates or active antifolate compounds.

Furthermore, the mild reactive conditions used in this invention permit the COR substituent, located on the divalent cyclic group (formula IV), to be selected and established prior to initiation of this process, and to remain as such, without modification, throughout the process.

The process of the present invention is shown below in Scheme II.

Scheme II

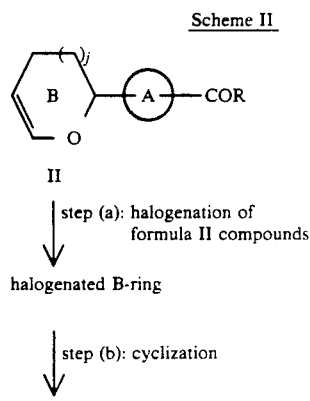

step (a): halogenation of formula II compounds halogenated B-ring step (b): cyclization -continued
Scheme II

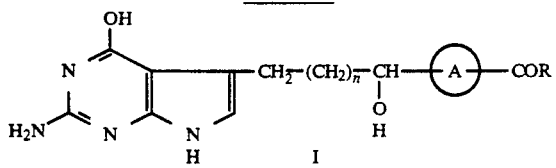

wherein

A, j, n and COR are as defined above.

The process of this invention is carried out by (a) halogenating a compound of formula II; and (b) reacting 2,4-diamino-6-hydroxypyrimidine with the reaction product from step (a), in the presence of a polar solvent. This process may be carried out as two independent steps or, preferably carried out, in situ, as a one-pot process, wherein step (b) is conducted immediately following the completion of step (a), without separating out the reaction product from step (a).

In step (a), generally known halogenating agents are employed. Particularly useful are brominating agents such as elemental bromine, N-bromosuccinimide, N-bromoacetamide and N-bromophthalimide. Of these, elemental bromine is preferred. Also of particular use are chlorinating agents such as elemental chlorine, N-chlorosuccinimide, and N-chlorophthalimide.

Compounds of formula I are then formed by the cyclization process shown in step (b). In step (b), cyclization of the 4-hydroxypyrido[2,3-d]pyrimidine ring system is accomplished by reacting 2,4-diamino-6-hydroxypyrimidine with the reaction product from step (a), in the presence of a polar solvent. Examples of suitable polar solvents include dimethylformamide (DMF), dimethyl sulfoxide (DMSO), acetone, acetonitrile, and alcohols, water and mixtures thereof. Of these, a mixture of acetonitrile and water is preferred.

Typically, step (b) may be accomplished as described above, but, preferably, the polar solvent will contain a salt of a weak acid (e.g. a buffering agent), for the purpose of reacting with hydrohalide formed during the cyclization of step (b). Sodium acetate is a preferred buffering agent.

Step (b) of this process is preferably operated in a temperature range from about 65° C. to about 85° C. Of course, the optimum operating temperature for a given reaction is easily found according to the routine skill of the organic chemist.

The necessary reaction times for steps (a) and (b) will vary, depending upon the starting materials used and the operating conditions, such as temperature. The optimum reaction time for a given process is, as always, a compromise which is found by considering the competing goals of throughput, which is favored by short reaction times, and maximum yield, which is favored by long reaction times.

Formula I compounds obtained from the product of this invention are readily isolated by ordinary procedures. For example, the previously heated mixture from step (b) is cooled to room temperature and the precipitate formed during this step is filtered and dried. When formula I compounds are used as intermediates, the recovered product does not need to be further purified. When the recovered product is to be used as a therapeutically active compound, the product may be further purified by methods commonly used in the organic chemical art.

Those formula I compounds wherein R is $OR^1$ and $R^1$ is either H or a carboxyl protecting group generally are intermediates which are useful for preparing novel or known 4-hydroxypyrrolo[2,3-d]-pyrimidine-L-glutamic acid derivatives, or for preparing other intermediates which are useful for synthesizing such L-glutamic acid derivatives. Numerous 4-hydroxypyrrolo[2,3-d]pyrimidine-L-glutamic acid derivatives are known to possess folate antimetabolic activity and are useful inter alia, as antineoplastic agents. See, e.g., U.S. Pat. Nos. 4,996,206, 4,997,838, and 5,106,974. However, the use of formula I compounds prepared via the process of this invention are not limited by these examples to such use.

Conversion of formula I intermediate compounds, when the R of COR is $OR^1$ and $R^1$ is either H or a carboxyl protecting group to active antineoplastic agents, is accomplished by methods well known to one or ordinary skill in the art. Typically, a protected L-glutamic acid derivative of the formula

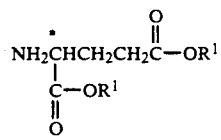

in which $R^1$ is a carboxyl protecting group and the configuration about the carbon atom designated * is L, is coupled with a formula I intermediate compound in the manner described in U.S. Pat. No. 4,684,653, using conventional condensation techniques for forming peptide bonds, but substituting the appropriate pyrrolo[2,3-d]pyrimidine for the pyrido[2,3-d]pyrimidine therein disclosed. The resulting 4-hydroxypyrrolo[2,3-d]pyrimidine is then subjected to hydrolysis to remove the $R^1$ carboxyl protecting groups.

Alternatively, a protected glutamic acid derivative of formula V may be coupled to the carboxyl group attached to an A-ring of formula II prior to subjecting the formula II compound to the process of this invention, using the abovementioned coupling technique. The resulting protected L-glutamic acid derivative may then be used in the process of this invention, resulting in a formula I intermediate which, upon hydrolysis of the $R^1$ carboxyl protecting groups, is an active 4-hydroxypyrrolo[2,3-d]pyrimidine antineoplastic agent.

Alternatively, a formula II compound, wherein R is $NHC^*H(COOR^1)CH_2CH_2COOR^1$, $R^1$ is H or a carboxyl protecting group and the designation "*" is as defined above, may be used directly in the process of this invention, yielding an active, 4-hydroxypyrrolo[2,3-d]pyrimidine antineoplastic agent. See, e.g., Example 4. Furthermore, the 9-hydroxyl substituent may then be removed by conventional methods such as catalytic hydrogenolysis, and the resulting products are also folate antimetabolites which possess antineoplastic activity. See, e.g., U.S. Pat. Nos. 4,996,206, 4,997,838 and 5,106,974.

The following examples further illustrate the process according to the present invention. The examples are not intended to be limiting to the scope of the invention, in any respect, and should not be so construed.

EXAMPLE 1

Methyl 4-(2,3-dihydrofuran-2-yl)benzoate

To a mixture of 269 mg (1.20 mmol) of palladium(II) acetate, 314 mg (1.20 mmol) of triphenylphosphine, 15.3 g (150 mmol) of lithium acetate dihydrate, and 13.9 g (50 mmol) of tetrabutylammonium chloride in 10 mL of dimethylformamide (DMF) which had been degassed under vacuum was added 13.10 g (50 mmol) of methyl 4-iodobenzoate and 17.50 g (150 mmol) of 2,3-dihydrofuran. The mixture was heated with stirring under nitrogen to about 80° C. for 4 h when complete conversion was obtained (TLC—silica, hexane-ethyl acetate 8:2). The mixture was cooled to room temperature and diluted with 200 mL of methyl t-butyl ether (MTBE) and 200 mL of water. The layers were separated and the organic phase washed with 2×100 mL of water. The combined aqueous phases were further extracted with 100 mL of MTBE. The organic phases were combined and treated with 3 g of activated carbon. The carbon was filtered and the filtrate washed with 2×100 mL of water, and dried ($Na_2SO_4$). Evaporation of the solvent afforded 9.29 g of crude product as a brown oil. Flash chromatography on silica gel (hexane-ethyl acetate 8:2) and short path distillation of the pooled fractions afforded 5.5 g (54%) of purified product, bp 165° C. (0.35 torr), as a low melting solid (mp about 252° C.), $^1$H NMR ($CDCl_3$) $\delta$2.56 (m, 1H), 3.12 (m, 1H), 3.91 (s, 3H), 4.97 (q, J=2.6 Hz, 1H), 5.57 (dd, J=2.7, 8.2 Hz, 1H), 6.47 (q, J=2.7 Hz, 1H), 7.42 (d, J=8.4 Hz, 2H), 8.03 (d, J=8.4 Hz, 2H); $^{13}$C NMR ($CDCl_3$) $\delta$37.9, 52.0, 81.6, 99.0, 125.4, 129.3, 129.8, 145.3, 148.2, 166.7; IR ($CHCl_3$) 3026, 2954, 1720, 1620, 1612, 1284, 1114, 1050 $cm^{-1}$; UV (EtOH) 235 ($\epsilon$12 483); MS(FD) m/z 204 ($M^+$). Anal. Calcd for $C_{12}H_{12}O_3$: C, 70.58; H, 5.92. Found: C, 70.33; H, 5.98.

EXAMPLE 2

4-(1-Hydroxy-2-[2-amino-4-hydroxypyrrolopyrimidin-5-y]-ethyl)benzoic acid methyl ester To a vigorously stirred mixture of 2.04 g (10 mmol) of methyl 4-(2,3-dihydrofuran-2-yl)benzoate in 15 mL of acetonitrile and 20 mL of water cooled to −10° C. was added dropwise a solution of 1.60 g (10 mmol) of bromine in 5 mL of acetonitrile. The mixture was stirred for 15 min after addition was complete. There was then added 1.26 g (10 mmol) of 2,4-diamino-6-hydroxypyrimidine and 2.46 g (30 mmol) of sodium acetate and the mixture was heated to about 75° C. for 2 h. After about 20 min the product began to precipitate. The mixture was cooled to room temperature and 20 mL of water was added. The product was filtered and dried, affording 2.3 g of crude product. The crude material was purified by slurry in DMF (140° C.), cooling, filtration, and reslurry in ether. Filtration of the ether suspension gave 1.54 g (47%) of the product as a white powder, mp>260° C. $^1$H NMR (DMSO-d6) $\delta$2.88 (m, 2H), 3.81 (s, 3H), 4.95 (m, 1H), 5.71 (d, J=4.7 Hz, 1H), 6.03 (s, 2H), 6.21 (br d, J=1.8 Hz, 1H), 7.41 (d, J=8.3 Hz, 2H), 7.86 (d, J=8.3 Hz, 2H), 10.28 (s, 1H), 10.64 (br s, 1H); MS(FD) m/z 328 ($M^+$). Anal. Calcd for $C_{16}H_{16}N_4O_4$: C, 58.37; H, 5.04; N, 17.29. Found: C, 58.53; H, 4.91; N, 17.06.

EXAMPLE 3

N-4-(2,3-dihydrofuran-2-yl)benzoyl-L-glutamic acid diethyl ester

A mixture of 21.7 g (50 mole) of 4-iodobenzoyl-L-glutamic acid, 0.314 g (1.2 mmol) of triphenylphosphine, 15.3 g (150 mmol) of lithium acetate, and 10.2 g (50 mmol) of tetrabutylammonium chloride in 10 mL of DMF was degassed under vacuum and covered with a nitrogen atmosphere. To the mixture was added 269 mg (1.20 mmol) of palladium(II) acetate and 17.5 g (250 mmol) of dihydrofuran. The mixture was heated to 75°–80° C. with stirring for 22 h, at which time the reaction was found to be complete by HPLC analysis of an aliquot. The cooled reaction mixture was poured into 500 mL of water and the resulting suspension extracted with 3×200 mL of ethyl acetate. The combined organic layers were washed with 4×200 mL of water, 200 mL of saturated NaCl solution, and dried ($Na_2SO_4$). Evaporation of the solvent gave 20.38 g of crude product as an oil. Flash chromatography of a 6.0 g portion (silica, ethyl acetate - hexane 1:1) afforded 1.42 g of purified N-4-(2,3-dihydrofuran-2-yl)-benzoyl-L-glutamic acid diethyl ester, mp 81°–82° C. $^1$H NMR ($CDCl_3$) $\delta$ 1.22 (t, J=7.2 Hz, 3H), 1.30 (t, J=7.2 Hz, 3H), 2.14 (m, 1H), 2.32 (m, 1H), 2.50 (m, 3H), 3.11 (m, 1H), 4.10 (q, J=7.2 Hz, 2H), 4.23 (q, J=7.2 Hz, 2H), 4.79 (m, 1H), 4.96 (q, J=2.5 Hz, 1H), 5.55 (m, 1H), 6.46 (q, J=2.4 Hz, 1H), 7.12 (d, J=7.4 Hz, 1H), 7.41 (d, J=8.2 Hz, 2H), 7.82 (d, J=8.2 Hz, 2H). IR ($CHCl_3$) 3420, 3012, 1732, 1662, 1622, 1613, 1523, 1496, 1377, 1050 $cm^{-1}$. UV (EtOH) 202 nm ($\epsilon$ 26 740), 233 nm ($\epsilon$ 14 900). MS(FD) m/z 375 ($M^+$). Anal. Calcd for $C_{20}H_{25}NO_6$: C, 63.99; H, 6.71; N, 3.73. Found: C, 63.84; H, 6.76; N, 3.99. An additional 1.6 g of product (48% pure by HPLC) was obtained from pooling of additional fractions.

EXAMPLE 4

N-4-(1-Hydroxy-2-[2-amino-4-hydroxypyrrolopyrimidin-5-yl]ethyl)benzoyl-L-glutamic acid diethyl ester To a mixture of 350 mg (0.93 mmol) of N-4-(2,3-dihydrofuran-2-yl)-benzoyl-L-glutamic acid diethyl ester, 3.0 mL of acetonitrile, and 3.0 mL water at room temperature was added dropwise with stirring a solution of 148 mg (0.93 mmol) of Bromine in 1 mL of acetonitrile until a yellow color persisted in the mixture. To the mixture was added 229 mg (0.93 mmol) of sodium acetate and 117 mg of 2,4-diamino-6-hydroxypyrimidine and the temperature was increased to 60° C. After 5 h the product began to precipitate from the reaction mixture. After 7 h the reaction was judged complete by HPLC analysis. Water (3 mL) was added and the mixture cooled to room temperature and filtered. The product was dried in vacuo at 50° C. to constant weight. There was obtained 348 mg (75%) of N-4-(1-hydroxy-2-[2-amino-4-hydroxypyrrolopyrimidin-5-yl]-ethyl) benzoyl-L-glutamic acid diethyl ester as a white solid. The material thus obtained was found to be identical with the product obtained in Example 2 by HPLC and NMR analysis. The material was further characterized as the p-toluenesulfonate salt, mp 221°–224° C. Anal. Calcd for $C_{31}H_{37}N_5O_{10}S$: C, 55.43, H, 5.55, N, 10.43. Found: C, 55.46; H, 5.78; N, 10.15.

We claim:

1. A process for preparing a 4-hydroxypyrrolo[2,3-d]pyrimidine derivative of the formula

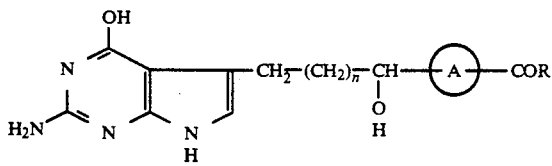

wherein
R is NHC*H(COOR$^1$)CH$_2$CH$_2$COOR$^1$ or OR$^1$;
R$^1$ is H or a carboxyl protecting group;
the configuration about the carbon atom designated * is L;
n is 0 or 1; and
A is an aryl group optionally having, in addition to the COR substituent, one or two substituents selected from the group consisting of halo, hydroxy, C$_1$-C$_4$ alkyl and C$_1$-C$_4$ alkoxy; or a salt thereof, which comprises
(a) halogenating a compound of the formula

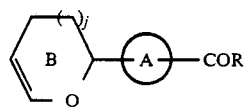

wherein
R, R$^1$, A and * are as defined above;
j is 0 or 1; and
(b) reacting 2,4-diamino-6-hydroxypyrimidine, or a salt thereof, with the reaction product from step (a), in the presence of a polar solvent.

2. The process of claim 1 which is a one-pot process.

3. A process according to claim 2 wherein said polar solvent is a mixture of acetonitrile and water.

4. A process according to claim 2 wherein said halogenation is accomplished by using elemental bromine.

5. A process according to claim 4 wherein R is OR$^1$;
R$^1$ is H or a carboxyl protecting group; and
A is phenyl-1,4-ylene.

6. A process according to claim 5 wherein R$^1$ is a carboxyl protecting group.

7. A process according to claim 6 wherein said carboxyl protecting group is ethyl.

8. A process according to claim 7 wherein j is 0.

9. A process according to claim 4 wherein R is NHC*H(COOR$^1$)CH$_2$CH$_2$COOR$^1$;
R$^1$ is H or a carboxyl protecting group; and
A is phenyl-1,4-ylene.

10. A process according to claim 9 wherein R$^1$ is a carboxyl protecting group.

11. A process according to claim 10 wherein said carboxyl protecting group is ethyl.

12. A process according to claim 11 wherein j is 0.

13. A process according to claim 2 wherein said halogenating agent is elemental chlorine.

14. A process according to claim 13 wherein R is OR$^1$;
R$^1$ is H or a carboxyl protecting group; and
A is phenyl-1,4-ylene.

15. A process according to claim 14 wherein R$^1$ is a carboxyl protecting group.

16. A process according to claim 15 wherein said carboxyl protecting group is ethyl.

17. A process according to claim 16 wherein j is 0.

18. A process according to claim 13 wherein R is NHC*H(COOR$^1$)CH$_2$CH$_2$COOR$^1$;
R$^1$ is H or a carboxyl protecting group; and
A is phenyl-1,4-ylene.

19. A process according to claim 18 wherein R$^1$ is a carboxyl protecting group.

20. A process according to claim 19 wherein said carboxyl protecting group is ethyl.

21. A process according to claim 20 wherein j is 0.

* * * * *